United States Patent [19]

Itoh et al.

[11] Patent Number: 5,362,420
[45] Date of Patent: Nov. 8, 1994

[54] LOW IMPEDANCE PRESSURE SENSITIVE ADHESIVE COMPOSITION AND BIOMEDICAL ELECTRODES USING SAME

[75] Inventors: Steven K. Itoh, Cottage Grove, Minn.; Timothy M. Dietz; Rosa Uy, both of St. Paul, Minn.

[73] Assignee: Minnesota Mining and Manufacturing Company, St. Paul, Minn.

[21] Appl. No.: 171,203

[22] Filed: Dec. 21, 1993

Related U.S. Application Data

[63] Continuation of Ser. No. 792,797, Nov. 15, 1991, abandoned.

[51] Int. Cl.[5] .......................... C08J 3/28; C08K 5/06
[52] U.S. Cl. ................................ 252/500; 525/326.9; 525/389; 524/386; 526/931
[58] Field of Search ..................... 252/500; 524/386; 525/326.9, 389; 526/931

[56] References Cited

U.S. PATENT DOCUMENTS

| | | | |
|---|---|---|---|
| Re. 31,454 | 12/1983 | Hymes | 128/641 |
| 3,998,215 | 12/1976 | Anderson et al. | 128/206 |
| 4,359,996 | 9/1982 | Engels | 128/640 |
| 4,391,278 | 7/1983 | Cahalan | 128/640 |
| 4,477,325 | 10/1984 | Osburn | 204/159 |
| 4,524,087 | 6/1985 | Engels | 427/2 |
| 4,554,924 | 11/1985 | Engels | 128/640 |
| 4,588,762 | 5/1986 | Mruk et al. | 524/45 |
| 4,699,146 | 10/1987 | Sieverding | 128/640 |
| 4,750,482 | 6/1988 | Sieverding | 128/156 |
| 4,771,783 | 9/1988 | Roberts | 128/640 |
| 4,830,776 | 5/1989 | Thompson | 252/500 |
| 4,846,185 | 7/1989 | Carim | 128/641 |
| 4,848,353 | 7/1989 | Engels | 128/640 |
| 4,931,282 | 6/1990 | Asmus et al. | 424/448 |
| 5,024,227 | 6/1991 | Schmid | 128/640 |
| 5,270,358 | 12/1993 | Asmus | 524/55 |
| 5,276,079 | 1/1994 | Duan et al. | 524/386 |

FOREIGN PATENT DOCUMENTS

| | | |
|---|---|---|
| 0085327 | 1/1983 | European Pat. Off. . |
| 0107376 | 9/1983 | European Pat. Off. . |
| 0297769 | 6/1987 | European Pat. Off. . |
| 0322098 | 11/1988 | European Pat. Off. . |
| WO91/90633 | 7/1991 | WIPO . |

OTHER PUBLICATIONS

Errede, "Molecular Interpretations of Sorption in Polymers Part I", *Advances in Polymer Science*, vol. 99, Springer-Verlag, Berlin Heidelberg Germany (pp. 22-36, 1991).

Rosiak et al., "Hydrogel Dreesings HDR", American Chemical Society Abstract, Aug. 1990 Meeting.

Rosiak et al., "Fast reaction of Irradiated Polymers—I. Crosslinking and Degradation of Polyvinylpyrrolidone", Radiat. Phys. and Chem. vol. 36, 6, pp. 747-755, 1990.

Linke et al., "PVP-A Versatile Specialty Polymer", *Polymer News*, vol. 12, pp. 232-237, 1987.

*Primary Examiner*—Paul Lieberman
*Assistant Examiner*—Michael P. Tierney
*Attorney, Agent, or Firm*—Gary L. Griswold; Walter N. Kirn; John H. Hornickel

[57] ABSTRACT

The present invention discloses a low impedance, water-absorbing, ionically-conductive, hydrophilic pressure sensitive adhesive composition comprising an ionically-conductive, hydrophilic, pressure sensitive adhesive hydrogel and crosslinked poly(N-vinyl lactam) in an amount sufficient to retain low electrical impedance and maintain hydrogel adhesion and cohesion during use of the composition in the presence of water and other moisture tending to plasticize the hydrogel. Crosslinked homopolymers and copolymers of poly(N-vinyl pyrrolidone) having Swelling Capacity of at least 15 milliliters of water per gram of poly(N-vinyl pyrrolidone) are preferred. Adhesion values upon removal from mammalian skin after about four hours of adhesion are not greater than initial adhesion removal values, demonstrating ease of removal of electrodes of the present invention from skin.

6 Claims, 1 Drawing Sheet

LOW IMPEDANCE PRESSURE SENSITIVE ADHESIVE COMPOSITION AND BIOMEDICAL ELECTRODES USING SAME

This is a continuation of application Ser. No.07/792,797 filed Nov. 15, 1991, now abandoned.

FIELD OF THE INVENTION

This invention relates to low impedance, ionically-conductive, hydrophilic pressure-sensitive adhesive compositions and the use of such compositions in biomedical electrodes.

BACKGROUND OF THE INVENTION

Modern medicine uses many procedures where electrical signals are received from or delivered to a mammalian patient's body through skin. The interface between medical equipment used in these procedures and the skin of the patient is usually some sort of biomedical electrode. Such biomedical electrodes typically include a conductor which must be connected electrically to the equipment, and a conductive medium adhered to or otherwise contacting mammalian skin.

Because all biomedical electrodes are based on the transmission of electrical signals to and from mammalian skin, good electrical conductivity is required, as free as possible from electrical impedance during a diagnostic, therapeutic, or electrosurgical procedure. Electrical impedance is disruptive to diagnostic or therapeutic procedures where low voltages or low currents are transmitted to or received from a patient's body. Lowering electrical impedance for biomedical defibrillation electrodes can lower the possibility of a less than effective electrical circuit at a moment of criticality for live-saving measures. Further, in the case of dispersive electrodes, an increase in impedance at one part of the contacting surface can increase the current density in places where the impedance is relatively lower. Electrical burns are a known problem in the use of dispersive electrodes when the current density in a region of the electrode becomes too high. Biocompatible, hydrophilic pressure-sensitive adhesive compositions (hereafter "PSA hydrogels") can be employed as the conductive medium for biomedical electrodes because such PSA hydrogels have excellent adhesion to a variety of types of mammalian skin, and good mechanical strength, and, with inclusion of an electrolyte, good electrical conductivity. Examples of PSA hydrogels based on copolymers plasticized with water and humectant that are preferred for biomedical electrodes are described in U.S. Pat. Nos. 4,524,087; 4,539,996; 4,554,924; and 4,848,353 (all Engel), which also describe constructions of biomedical electrodes suitable for use as dispersive biomedical electrodes. Also, EPO Publication 0 322 098 (Duan) describes another PSA hydrogel based on plasticized poly(N-vinyl lactam) which can be used as the conductive medium for biomedical electrodes. The disclosures of all of the co-assigned Engel patents and Duan European Patent Publication are incorporated by reference herein.

Mechanical and electrical properties of a PSA hydrogel useful in a biomedical electrode are dependent on the content of water or moisture in the PSA hydrogel as formed and then as stored and used. In each of the Engel patents and the Duan publication, water is employed in the formation of the PSA hydrogel and water is required for electrical conductivity by interaction with an electrolyte. These PSA hydrogels are one phase compositions which are both hypoallergenic pressure sensitive adhesives and ionically-conductive media for transmission or reception of electrical signals.

By contrast, U.S. Pat. No. 4,588,762 (Mruk et al.) describes a heterogenous, pressure-sensitive, electrically conductive adhesive for disposable biomedical electrodes, consisting of two phases: a viscoelastic polymeric adhesive phase and an electrically conductive aqueous phase containing a water receptive polymer, a humectant, and an electrolyte. The humectant is present in the aqueous composition phase to minimize evaporation of water or moisture present during formation of the adhesive from the aqueous zones extending through the thickness of the composition. However, there is no electrical conductivity in the viscoelastic polymeric adhesive phase. Further, a two phase pressure-sensitive system described by Mruk et al., having regions without electrical conductivity is otherwise unsuitable for dispersive biomedical electrodes.

European Patent Publication 0 085 327 (Cahalan et al.) describes electrically conductive compositions useful for biomedical electrodes wherein the conductive composition comprises an interpenetrating polymer network consisting essentially of a hydrophilic cross-linked polymer formed from a water soluble monomer (such as an N-sulfohydrocarbon-substituted acrylamide, hydroxymethylmethacrylate, and potassium acrylate polymers) and a hydrophilic polymer which is not crosslinked (such as polyacrylic acid, polyvinylpyrrolidone, and non-crosslinked N-sulfohydrocarbon-substituted acrylamides), a humectant, and water.

Incorporation of water swellable polymers into other materials has been used for bandage and wound dressing type products.

European Patent Publication 0 297 769 (Cilento) discloses a pressure sensitive acrylic adhesive mass which is made hydrophilic by blending one or more water moisture absorbing, water moisture transmitting substances into the acrylic mass. These substances can be water soluble or swellable hydrocolloids (such as cellulosics, gums and the like) or super absorbents (such as substantially water insoluble, starch-acylonitrile graft copolymers, water insoluble, cross-linked sodium carboxymethylcellulose, or water insoluble, crosslinked dextran). European Patent Publication 0 107 376 (Thompson et al.) discloses polypyrrolidone gel dressings prepared by dissolving between 15% and 25% by weight of polyvinylpyrrolidone in water and cross-linking the polypyrrolidone by means of ionizing radiation. Various reinforcing materials, such as nylon gauze, cellulose, reticulated polyethylene or polypropylene, can be included as reinforcing agents.

U.S. Pat. No. 4,477,325 (Osburn) discloses a skin barrier composition of a ethylene and vinyl acetate copolymer (EVA) resin, at least one water absorbing particulate hydrocolloid polymer, and a water-insoluble, dry tack-providing elastomer such polyisobutylene, to be useful as an ostomy appliance and the like. After mixing and molding, the composition is subjected to ionizing irradiation to form cross-linked polymer networks.

SUMMARY OF THE INVENTION

The problem of controlling both mechanical and electrical properties of a PSA hydrogel is solved by the present invention by controlling the water or moisture content during formation, storage, and use. While electrical impedance can be reduced in a PSA hydrogel by increasing water or moisture content in the PSA hydrogel, cohesion of the PSA hydrogel unfortunately decreases with increasing water or moisture content.

The present invention unexpectedly can optimize both mechanical and electrical properties of a PSA hydrogel for use as a biomedical electrode, and particularly a dispersive biomedical electrode, by introducing crosslinked poly(N-vinyl lactam) into the PSA hydrogel to control the water or moisture content of the PSA hydrogel. The present invention provides a PSA hydrogel having both good electrical properties, i.e., low impedance and good mechanical properties, i.e., good skin adhesion and good cohesive strength.

The present invention provides a low impedance, water-absorbing, ionically-conductive, hydrophilic pressure-sensitive adhesive composition comprising an ionically-conductive, hydrophilic, pressure sensitive adhesive hydrogel and crosslinked poly(N-vinyl lactam) present in an amount sufficient to retain low electrical impedance and maintain hydrogel adhesion and cohesion during use in the presence of mammalian body fluids tending to plasticize the PSA hydrogel.

The present invention also provides a biomedical electrode having a low impedance, water-absorbing, ionically-conductive, hydrophilic pressure-sensitive composition in contact with a means for electrical communication with electrical equipment.

The present invention also provides a method of using a biomedical electrode to provide electrical communication between mammalian skin and electrical instrumentation. The method comprises the steps of adhering a biomedical electrode of the present invention to skin of a mammal, and connecting said biomedical electrode to electrical instrumentation to perform the diagnostic, therapeutic, or electrosurgical medical procedure. The step of adhering for a diagnostic or therapeutic medical procedure occurs in an area where a diagnostic or therapeutic medical procedure is to occur. The step of adhering for an electrosurgical medical procedure occurs in an area away from the electrosurgical incision location.

A feature of the present invention is that the crosslinked, hydrophilic, biocompatible water-absorbing composition is compatible with methods to prepare the PSA hydrogel from monomers or pre-polymer systems, minimizing processing difficulties.

Another feature of the present invention is that use of poly(N-vinyl lactam) reduces the presence of monomeric components in the PSA hydrogel during processing of the PSA hydrogel.

Another feature of the present invention is that the presence of poly(N-vinyl lactam) can permit alteration of the formulation of the PSA hydrogel, affecting electrical impedance of the resulting composition without substantially altering adhesion and cohesion.

Another feature of the present invention is that the PSA hydrogel minimizes leaving residue on skin after use is concluded because crosslinked poly(N-vinyl lactam) absorbs water. This water absorption minimizes plasticization of the PSA hydrogel during use. Otherwise, tack and adhesion to skin would increase over time with resulting difficulty or discomfort during removal of the PSA hydrogel from skin.

An advantage of the present invention is that the PSA hydrogel can retain preferred mechanical properties while crosslinked poly(N-vinyl lactam) absorbs water and moisture from skin or skin openings of a patient during use of a biomedical electrode.

Embodiments of the invention are described with reference to the drawing.

EMBODIMENTS OF THE INVENTION

PSA Hydrogel

Figure 1:
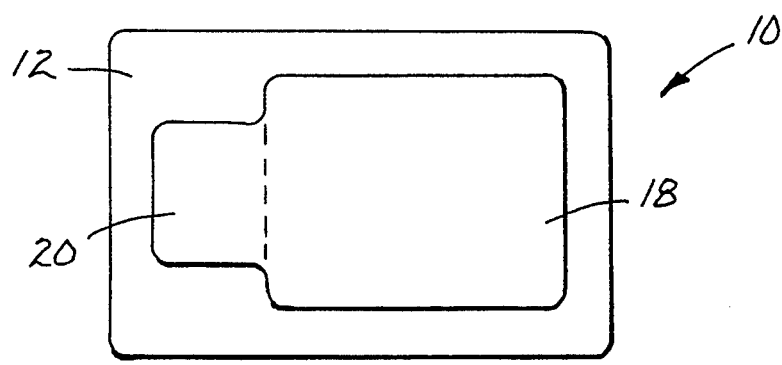
FIG. 1 is a top plan view of a biomedical electrode used for diagnosis of heart conditions of a mammalian patient.

The PSA hydrogel useful for the present invention can be any biocompatible, ionically-conductive, hydrophilic pressure-sensitive adhesive composition currently described for use as a conductive adhesive for biomedical electrodes. Nonlimiting examples of conductive adhesives capable of adhering to mammalian skin include those adhesives disclosed in the Engel patents identified above, the Duan European Patent Publication identified above, and adhesives disclosed in U.S. Pat. Nos. Re. 31,454 (Hymes); 4,391,278 (Cahalan); 4,699,146 and 4,750,482 (both Sieverding).

Thus, nonlimiting examples of PSA hydrogels include compositions prepared from (a) partially neutralized acrylic acid homopolymers and copolymers, copolymers of (N-vinyl lactam and a multi-ethylenically unsaturated compound, copolymers of (N-vinyl lactam) and a carboxylic acid, or an interpenetrating polymer network of hydrophilic crosslinked polymer from a water soluble monomer and a hydrophilic polymer which is not crosslinked; (b) humectant, and (c) water.

PSA hydrogels useful for the present invention can have an initial adhesion to skin ranging from about 20 grams/2.54 cm to about 80 grams/2.54 cm using a skin adhesion test described below.

Of the possible PSA hydrogels useful for the present invention, conductive adhesives disclosed in U.S. Pat. Nos. 4,539,996 and 4,524,087 (both Engel) are preferred. These conductive adhesives have an initial adhesion to skin of about 15–40 grams/2.54 cm.

The presently preferred formulation of PSA hydrogel comprises about 14–26 weight percent of acrylic acid, about 0.04–0.08 weight percent of 2,2-dimethoxy-2-phenylacetophenone, about 0.2–2 weight percent of triethyleneglycolbismethacrylate, about 2–19 weight percent of alkali metal hydroxide, about 10–30 weight percent of water, and about 45–75 weight percent of glycerin.

Crosslinked Poly (N-vinyl lactam)

Crosslinked poly(N-vinyl lactam) is present in the PSA hydrogel composition in an amount sufficient to retain continued low electrical impedance and maintain hydrogel adhesion and cohesion during use. Desirably, the crosslinked poly(N-vinyl lactam) can comprise from about 0.5 to about 3 percent by weight of the PSA hydrogel composition. Preferably, crosslinked poly(N-vinyl lactam) can comprise from about 1 to about 2 percent by weight of the PSA hydrogel composition.

Poly(N-vinyl lactam) can be a noncrosslinked homopolymer or a noncrosslinked copolymer containing N-vinyl lactam monomeric units, which after crosslinking, such as by irradiation, can swell in water, moisture or other body exudate which otherwise affects mechanical or electrical properties of a PSA hydrogel used in a biomedical electrode.

N-vinyl lactam monomeric units comprise a majority of total monomeric units of the polymer.

Nonlimiting examples of N-vinyl lactam monomers are N-vinyl-2-pyrrolidone; N-vinyl-2-valerolactam; N-vinyl-2-caprolactam; and mixtures of any of the foregoing. Preferably, the N-vinyl lactam is N-vinyl-2-pyrrolidone. Preferably, the poly(N-vinyl lactam) is a homopolymer of N-vinyl-2-pyrrolidone.

Nonlimiting examples of non-N-vinyl lactam comonomers useful with N-vinyl lactam monomeric units include N,N-dimethylacrylamide, acrylic acid, methacrylic acid, hydroxyethylmethacrylate, acrylamide, 2-acrylamide-2-methyl-1-propane sulfonic acid or its salt, and vinyl acetate.

The N-vinyl lactam monomeric units comprise no less than about 50 weight percent of the monomeric units present in the poly(N-vinyl lactam) in solid state form. More preferably, the N-vinyl lactam monomeric units comprise 70 to 100 percent by weight of the poly(N-vinyl lactam) and most preferably 90 to 100 percent by weight of the poly(N-vinyl lactam).

Noncrosslinked poly(N-vinyl lactam) homopolymer and poly(N-vinyl pyrrolidone)/poly vinyl acetate copolymers are commercially available. Nonlimiting examples of commercially available poly(N-vinyl pyrrolidone) useful for the present invention include Aldrich Chemical Co. of Wilwaukee, Wis., BASF of Parsippany, N.J., GAF of Wayne, N.J., and Dan River Corporation of Danville, Va. and Spectrum Chemical Manufacturing Corporation of Gardena, Ca.

Poly(N-vinyl lactam) can have a Fikentscher K-value of at least K-15 and preferably at least K-60, and most preferably at least K-90. Fikentscher K-values are described in Molyneaux, Water-Soluble Polymers: Properties and Behavior, Vol. 1, CRC Press, 1983, pp. 151–152.

After exposure to ionizing radiation, poly(N-vinyl lactam) can have a Swelling Capacity, S, milliliters of liquid sorbed per gram of polymer, of at least about 15 in water, preferably at least about 30 in water, and most preferably at least about 40 in water.

Swelling Capacity correlates to a measurement of polymer swelling as a function of chemical crosslinking units in poly(N-vinyl lactam), according to the equation:

$$S = C(\lambda^{\frac{1}{3}} - \lambda_0^{\frac{1}{3}})$$

where S is a measurement of water sorbed per gram of polymer, C is a constant characteristic of the polymer, i.e., milliliters of water sorbed per gram of polymer, $\lambda$ is the average number of backbone carbon atoms in the polymer segments between crosslinked junctions, and $\lambda_0$ is the average number of backbone carbon atoms in the polymer segments between crosslinked junctions when S is zero. Swelling capacity and this equation are discussed in Errede, "Molecular Interpretations of Sorption in Polymers Part I", *Advances in Polymer Science* Vol. 99, Springer-Verlag, Berlin Heidelberg Germany (pp. 22–36, 1991), the disclosure of which is incorporated by reference.

Poly(N-vinyl lactam) useful in the present invention can be in any form susceptible to being crosslinked, but preferably is in a solid state form. Nonlimiting examples of solid state forms include particles, pellets, sheets, strands, fibers, membranes, films, and other three dimensional functional forms. Preferably, poly (N-vinyl lactam) is in the form of particles of a size from about 0.1 micrometers to about 250 micrometers and preferably from about 10 micrometers to about 75 micrometers.

Crosslinking of Poly(N-Vinyl Lactam)

Crosslinked poly(N-vinyl lactam) compositions can be prepared using free-radical polymerization methods employing chemical crosslinking agents such as that disclosed in U.S. Pat. No. 4,848,353 (Engel), U.S. Pat. No. 4,931,282 (Asmus et al.) or EPO Publication 0 322 098 (Duan) or using ionizing radiation such as that disclosed in co-pending, co-assigned U.S. patent application Ser. No. 07/792,442 (Docket No. 45911USA1A), the disclosures of such methods of crosslinking being incorporated by reference as if rewritten herein.

Preferably, poly(N-vinyl lactam) in any solid form is subjected to ionizing radiation from a high-energy source. Nonlimiting examples of ionizing radiation include alpha, beta, gamma, electron-beam, and x-ray radiation. Of these sources or ionizing radiation, electron-beam irradiation and gamma irradiation are preferred. Sources of electron-beam radiation are commercially available, including an Energy Sciences Inc. Model CB-150 Electrocurtain Electron Beam Processor. Sources of gamma irradiation are commercially available from Atomic Energy of Canada, Inc. using a cobalt-60 high-energy source.

Ionizing radiation dosages are measured in megarads (mRad) or kilograys (kGy). Doses of ionizing radiation can be administered in a single dose of the desired level of ionizing radiation or in multiple doses which accumulate to the desired level of ionizing radiation. The dosage of ionizing radiation cumulatively can range from about 25 kGys to about 400 kGys and preferably from about 25 kGys to about 200 kGys. Preferably, ionizing radiation can achieve the desired level of crosslinking of N-vinyl lactam moieties in poly(N-vinyl lactam) when the cumulative dosage of ionizing radiation exceeds 100 kGys (10 mRads).

Poly(N-vinyl lactam) can be irradiated in a solid form with ionizing radiation in a package or container where the temperature, atmosphere, and other reaction parameters can be controlled.

Temperature can range from about $-80°$ C. to about 100° C. and preferably from about 10° C. to about 35° C.

The atmosphere can be air or preferably an inert atmosphere such as nitrogen.

The line speed for electron-beam irradiation can be about 15 meters/minute.

The pressure in the container can be atmospheric, elevated or depressed. Preferably it is atmospheric.

Depending upon the control of the irradiation conditions, poly(N-vinyl lactam) can be irradiated in a batch or continuous process.

Crosslinked poly(N-vinyl lactam) is biocompatible with mammalian skin and hydrophilic without dissolving in water, moisture, or bodily fluids.

Biomedical Electrodes

Biomedical electrodes employing compositions of PSA hydrogel and poly(N-vinyl lactam) according to the present invention are useful for diagnostic, therapeutic, electrosurgical, or other medical purposes. In its most basic form, a biomedical electrode comprises a conductive medium contacting mammalian skin and a means for electrical communication interacting between the conductive medium and electrical diagnostic, therapeutic, or electrosurgical equipment.

Among the diagnostic and therapeutic procedures using biomedical electrodes are transcutaneous electronic nerve stimulation (TENS) devices used for pain management, neuromuscular stimulation (NMS) used for treating conditions such as scoliosis, and monitors of electrical output from body functions, such as electrocardiogram (EKG) used for monitoring heart activity and diagnosing heart abnormalities.

Figure 2:
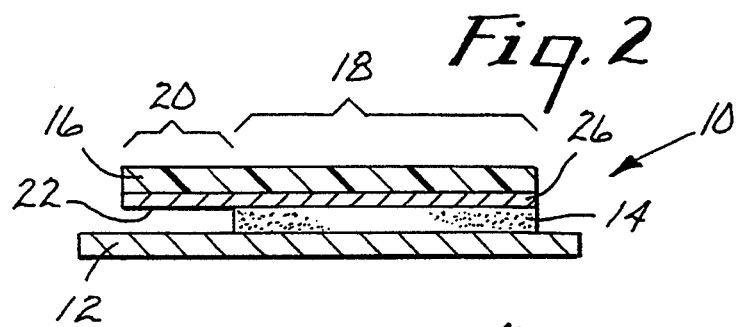
FIG. 2 is a cross-sectional view of the biomedical electrode of FIG. 1.

FIGS. 1 and 2 show either a disposable diagnostic electrocardiogram (EKG) or a transcutaneous electrical nerve stimulation (TENS) electrode 10 on a release liner 12. Electrode 10 includes a field 14 of a biocompatible and adhesive conductive medium for contacting mammalian skin of a patient upon removal of protective release liner 12.

Electrode 10 includes means for electrical communication 16 comprising a conductor member having a conductive interface portion 18 contacting field 14 of conductive medium and a tab portion 20 not contacting field 14 of conductive medium for mechanical and electrical contact with electrical instrumentation (not shown). Means 16 for electrical communication includes a conductive layer 26 coated on at least the side 22 contacting field 14 of conductive medium.

It is foreseen that a typical EKG conductor member 16 will comprise a strip of material having a thickness of about 0.05–0.2 millimeters, such as polyester film and have a coating 26 on side 22 of silver/silver chloride of about 2.5–12 micrometers, and preferably about 5 micrometers thick thereon. Presently preferred is a polyester film commercially available as "Mellinex" 505–300, 329, 339 film from ICI Americas of Hopewell, Va. coated with a silver/silver chloride ink commercially available as "R-300" ink from Ercon, Inc. of Waltham, Mass. A TENS conductor member 16 can be made of a nonwoven web, such as a web of polyester/cellulose fibers commercially available as "Manniweb" web from Lydall, Inc. of Troy, N.Y. and have a carbon ink layer 26 commercially available as "SS24363" ink from Acheson Colloids Company of Port Huron, Mich. on side 22 thereof. To enhance mechanical contact between an electrode clip (not shown) and conductor member 16, an adhesively-backed polyethylene tape can be applied to tab portion 20 on the side opposite side 22 having the conductive coating 26. A surgical tape commercially available from 3M Company as "Blenderm" tape can be employed for this purpose.

Another type of therapeutic procedure, which can employ a biomedical electrode having a low impedance PSA composition of the present invention, is the dispensing of electrical energy to the chest cavity of a mammalian patient to defibrillate abnormal heart beats of the patient. Delivery of a high (e.g., 2000 volts) voltage, high (e.g., 40 amps) current electrical charge through one biomedical electrode and receipt of that electrical charge through another biomedical electrode completes the electrical circuit. An example of an electrode useful for defibrillation is disclosed in U.S. Pat. No. 3,998,215 (Anderson et al.), which is incorporated herein by reference.

Another type of therapeutic procedure involving application of electrical current to skin of a patient is iontophoresis, which delivers an iontophoretically active pharmaceutical to or through mammalian skin with aid of an electrical current.

Electrosurgery can use a biomedical electrode using a low impedance PSA composition of the present invention. In this instance, the biomedical electrode serves to receive in a dispersed fashion electrical signals introduced to the patient at an incision site using an electrosurgical cutting electrode. An electro-surgical system usually comprises a generator providing high-frequency alternating current on demand under monitored conditions, the cutting electrode having an extremely high-current density and a flat dispersive biomedical electrode having a very large surface area to provide a low-current density. The dispersive biomedical electrode is placed in intimate and continuous contact with a portion of the mammalian skin which is not subject to the surgical procedure. The alternating current circuit is completed through the body of the patient between the dispersive biomedical electrode and the cutting electrode. Disconnection of the dispersive electrode either from contacting the patient or from the generator could subject the patient to electrical burns where the alternating current circuit leaves the body of the patient.

Figure 3:
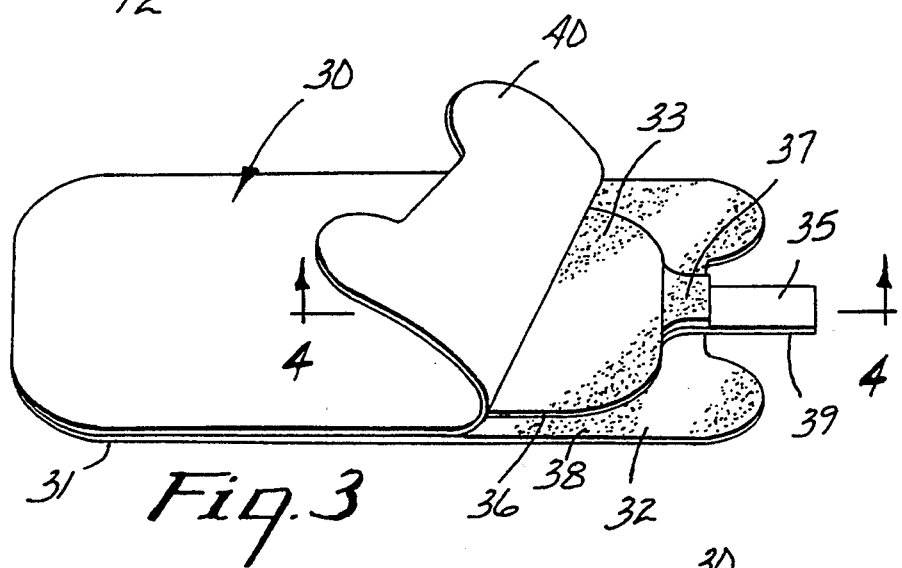
FIG. 3 is a perspective view of a dispersive biomedical electrode used for receiving electrical current during electrosurgery.
Figure 4:
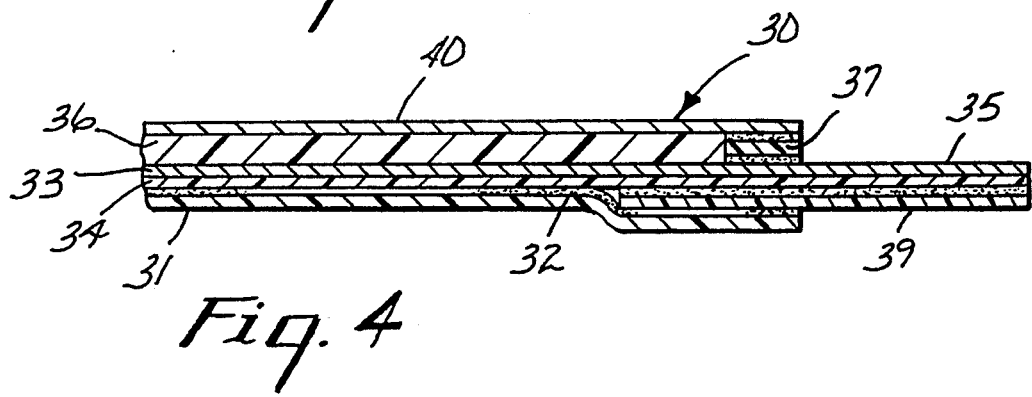
FIG. 4 is a cross-sectional view of the dispersive biomedical electrode of FIG. 3.

A dispersive electrode is seen in FIGS. 3 and 4. Dispersive electrode 30 comprises an insulating backing 31 coated on one surface with a biocompatible pressure sensitive adhesive 32. The backing 31 can be a closed cell polyethylene foam. An electrode plate 33 adheres to a portion of the biocompatible pressure sensitive adhesive 32. The electrode plate 33 can be an aluminum foil on a conformable polymeric backing 34, e.g., polyester, having aluminum deposited on one surface. The electrode plate 33 has an integrally associated connector tab 35 suited to electrically connect the dispersive electrode 30 to a leadwire which in use is connected to an electrosurgery generator. A field of electrically-conductive adhesive 36 of the present invention coats the entire electrically-conductive surface of electrode plate 33 except the connector tab 35. An insulating strip 37 double coated with pressure sensitive adhesive covers that portion of the surface of the connecting tab 35 which underlies the backing 31 and biocompatible pressure sensitive adhesive 32. The backing 31 and biocompatible pressure sensitive adhesive 32 have an apron 38 extending beyond the periphery of the electrode plate 33 and electrically-conductive adhesive 36. Apron 38 and insulating strip 37 serve to insulate the electrode plate 33 from direct contact with a patient's skin, thereby avoiding thermal burns and from contact with other conductors (e.g., blood or water) which may result in an electrical short circuit. Supporting connecting tab 35 is a reinforcing layer 39 of nonwoven polyester contacting adhesive 32 and having a single coated adhesive layer contacting tab 35. An optional release liner 40 can be used to protect adhesives 32 and 36 prior to use.

Preferably, to achieve excellent adhesion and low impedance electrical contact with a patient's skin (avoiding hot spots or loss of contract due to motion), the surface area of plate 33 and adhesive 36 of the present invention are each about 130 cm$^2$. Preferably, the adhesive 36 of the present invention is coated about 0.5 mm thick.

Other examples of biomedical electrodes which can use low impedance pressure sensitive adhesive compositions of PSA hydrogel and poly(N-vinyl lactam) according to the present invention as conductive adhesive fields include electrodes disclosed in U.S. Pat. No. 4,527,087; 4,539,996; 4,554,924; 4,848,353 (all Engel);

4,846,185 (Carim); 4,771,713 (Roberts); 4,715,382 (Strand); 5,012,810 (Strand et al.); co-pending and co-assigned U.S. patent application Ser. No. 07/686,049; co-pending and co-assigned U.S. patent application Ser. No. 07/688,138, the disclosures of which are incorporated by reference herein.

When used for diagnostic EKG procedures, electrodes shown in FIGS. 1 and 2 are preferred. When used for monitoring electrocardiogram (ECG) procedures, electrodes disclosed in U.S. Pat. No. 5,012,810 and U.S. application Ser. No. 07/686,049 are preferred. When used for defibrillation procedures or electrosurgical procedures, electrodes shown in FIGS. 3 and 4 or disclosed in U.S. Pat. Nos. 4,539,996 and 4,848,353 are preferred.

In some instances, the means for electrical communication can be an electrically conductive tab extending from the periphery of the biomedical electrodes such as that seen in U.S. Pat. No. 4,848,353 or can be a conductor member extending through a slit or seam in an insulating backing member, such as that seen in U.S. Pat. No. 5,012,810. Otherwise, the means for electrical communication can be an eyelet or other snap-type connector such as that disclosed in U.S. Pat. No. 4,846,185. Further, the means for electrical communication can be a lead wire such as that seen in U.S. Pat. No. 4,771,783. Regardless of the type of means for electrical communication employed, low impedance PSA hydrogel compositions of the present invention can reside as a field of conductive adhesive on a biomedical electrode for diagnostic, therapeutic, or electrosurgical purposes.

Method of Preparing Low Impedance PSA Hydrogel Compositions

The preparation of low impedance PSA hydrogel compositions of the present invention follows processes employed for the formation of PSA hydrogels with the addition of crosslinked poly(N-vinyl lactam) in amounts sufficient to provide continued low electrical impedance during use. Thus, any of the methods of preparation of a PSA hydrogel can be employed if the addition of crosslinked poly(N-vinyl lactam) is not disruptive to the formation of the hydrogel. Presently preferred methods of preparation include those methods disclosed in all Engel patents and the Asmus et al. patent described above.

For example, a method of preparing a low impedance PSA hydrogel composition of the present invention can employ a minimum number of ecologically compatible manufacturing steps. The solid, radiation-crosslinked poly(N-vinyl lactam) is mixed and equilibrated with water and humectant. In a separate container PSA hydrogel ingredients are mixed together with any other optional additives in water. The two mixtures are then combined and equilibrated, then cast onto a surface of a substrate, which can be an inert substrate such as a liner for storage before further processing or a surface designed for ultimate use, such as a means for electrical communication having an electrically conductive surface for use as a biomedical electrode. Then the cast mixture is cured in the manner described in the Engel patents, and particularly in Example 1 of U.S. Pat. No. 4,524,087 (Engel), except that an inert chamber is not required. A product liner can optionally be laminated over the field of low impedance PSA hydrogel to protect that field from contamination.

A coating of low impedance, PSA hydrogel composition of the present invention can be applied to a substrate surface. Coating thickness can range from about 0.25 mm to about 1 mm and preferably from about 0.4 mm to about 0.6 mm. With this coating, a low profile and conformable biomedical electrode can be made.

The method can be prepared in a batch process or in a continuous line process. If prepared by a continuous process, the laminate of a liner, field of cohesive, pressure-sensitive adhesive composition, and substrate can be wound on a roll for bulk packaging and further processing or can be cut using dies known to those skilled in the art into individual units, such as biomedical electrodes or biomedical electrode subassemblies, for further processing. U.S. Pat. No. 4,795,516 (Strand) and U.S. Pat. No. 4,798,642 (Craighead et al.), which are incorporated by reference herein, disclose processes and equipment useful for a continuous manufacture of biomedical electrodes involving the dispensing of strips of material from rolls and overlaying such strips in a registered continuous manner in order to prepare a strip of electrodes. Further, co-pending, co-assigned U.S. patent application Ser. Nos. 07/686,049 and 07/688,138 disclose methods of preparing biomedical electrode constructions in a continuous strip subassembly.

For example, one method of continuous strip assembly can be the coating of an aqueous mixture of low impedance, PSA hydrogel composition of the present invention on an electrically conductive surface about 8.9 cm wide, with the coating applied to about the center 5.1 cm section of such width. After photoinitiated polymerization of the mixture, the coated electrically conductive surface can be bisected along the strip and also cut orthogonally at about 2.54 cm intervals, yielding a number of electrodes 10 seen in FIG. 1 having dimensions of about 2.54 cm×4.4 cm with a conductive interface portion 18 of 2.54 cm×2.54 cm and a tab portion 20 of 2.54 cm×1.9 cm.

As another example, one method of assembly for a dispersive electrode can be the coating of an aqueous mixture of low impedance, PSA hydrogel composition of the present invention on a web having an electrically conductive surface about 24 cm wide, with the coating applied to an 18.4 cm section on one side of the web. The coating is photopolymerized. The web is then orthogonally cut and laminated to a conformable backing, yielding an electrode seen in FIG. 3 having an overall dimension of 10 cm×23 cm.

The following examples further describe embodiments of the invention without limiting the scope of the invention thereto.

EXAMPLES

Example 1—Preparation of Crosslinked Poly(N-vinyl lactam)

Approximately 100 grams of noncrosslinked poly(N-vinyl pyrrolidone) commercially available from BASF of Parsippany, N.J. in a solid state form of particles having a size from about 10 micrometers to about 75 micrometers were placed in a resealable plastic bag, purged with nitrogen for 15 minutes, and irradiated with ionizing radiation of about 140 kGys to about 160 kGys of gamma radiation using a Cobalt 60 gamma irradiation source in an Atomic Energy of Canada, Inc. Model JS-7500 equipment at ambient temperature and pressure.

Examples 2-3 and Comparative Example 4—Comparison of Impedance in Biomedical Electrodes Ingredients and quantities to prepare low impedance conductive adhesives of the present invention and a conventional conductive adhesive are listed in Table 1. For Examples 2 and 3, 2 grams of crosslinked poly(N-vinylpyrrolidone) prepared according to Example 1 was added to 12 grams of water in a container with stirring. Glycerin was added to the mixture. In a separate container, acrylic acid, 2,2-dimethoxy-2-phenylacetophenone, (benzildimethylketal commercially available as Irgacure 651 from Ciba Geigy), and triethyleneglycolbismethacrylate (TEGBM) were mixed. Potassium hydroxide was subsequently added to the acrylic acid solution and then the remainder of water was added to the solution to dissolve the potassium hydroxide. The acrylic acid mixture was then mixed with the poly(N-vinyl pyrrolidone) mixture and this combined mixture was equilibrated overnight prior to curing. Samples were coated on a polyester liner and then cured via ultraviolet light operated at 300-400 nm, (preferably 350 nm), and 1.2 milliwatts/cm$^2$ intensity for 5 minutes at ambient conditions.

Comparison example 4 represents a commercially available electrode and was prepared in the same manner as Examples 2 and 3 except that no poly(N-vinyl pyrrolidone) was added to the precursor mixture and that water and glycerin from that mixture were added to the acrylic acid solution before adding the potassium hydroxide. Coating and curing were the same.

Table 1 shows the formulations and Table 2 shows the electrical performance and adhesive performance of electrodes so prepared according to the following Impedance test and Skin Adhesion test.

Skin Adhesion Test

Adhesive sheets on a polyester backing were cut into 2.54 cm×7.5 cm strips such that each strip was completely covered on one side with the test adhesive. The strips were applied on the backs of human subjects perpendicular to the backbone and rolled with a 2 kg. roller to insure uniform application. The strips were removed from the back promptly after application using a mechanical pulling device termed an adhesion tester. This device consists of a motor driven screw drive which pulls a 11.4 kg test line to which is attached a metal clip which is 2.54 cm wide. The metal clip is attached to each strip at its 2.54 cm width during pulling testing. Strips were pulled in a plane parallel (180°) to the back and parallel to the long axis of the strip at a rate of 13/14 cm/min. The adhesion is reported in grams/2.54 cm and based on an average of values from initiation of peel to entire removal.

Impedance Test

The impedance was measured using a Hewlett Packard Model 4800A Vector Impedance Meter, two 15.24 cm lead wires, and a stainless steel cylinder. The stainless steel cylinder had a circular cross section with a diameter of 3.81 cm. The weight of the cylinder was 454 grams. One lead wire connected the meter to an exposed portion of the electrode conductor. The other lead wire connected the meter to the cylinder. The circular area of one end of the cylinder was laminated to an area of exposed conductive adhesive on the electrode making sure no bubbles were present between the adhesive and the cylinder. The electrode was placed on a level surface with the conductive adhesive facing up and the cylinder on top of the electrode. The impedance was measured at a frequency of 500,000 Hz. The impedance value was divided by the thickness of the conductive adhesive to arrive at a value in ohms/0.0254 mm.

TABLE 1

| Ingredients (grams) | Example 2 | Example 3 | Comparison Example 4 |
|---|---|---|---|
| Acrylic acid | 22 | 20 | 24 |
| Benzildimethylketal | 0.06 | 0.06 | 0.06 |
| TEGBM | 0.25 | 0.3 | 0.2 |
| Water | 24 | 24 | 10.5 |
| KOH | 6.43 | 5.84 | 7.01 |
| Glycerin | 45.26 | 47.8 | 58.23 |
| Crosslinked PVP | 2 | 2 | 0 |

TABLE 2

| Property | Example 2 | Example 3 | Comparison Example 4 |
|---|---|---|---|
| Skin Adhesion (grams/2.54 cm) | 30.7 | 42.9 | 29.1 |
| Impedance (Ohm/0.0254 mm) | 0.177 | 0.158 | 1.19 |

A comparison of the results of Examples 2 and 3 with Comparison Example 4 shows that impedance can be significantly reduced without significant changes in skin adhesion.

Impedance data show that addition of poly(N-vinyl lactam) greatly reduces impedance over the area of adhesive coverage and thickness by one/sixth compared with commercially available conductive adhesives. Thus, electrical properties of biomedical electrodes can be greatly improved by the addition of crosslinked poly(N-vinyl lactam) to commercially available, ionically-conductive PSA hydrogels.

Examples 5-11 and Comparison Example 12—Comparison of Mammalian Skin Adhesion in Biomedical Electrodes Ionically-conductive pressure sensitive adhesives were prepared for Examples 5-11 using the ingredients shown in Table 3. The crosslinked poly(N-vinylpyrrolidone) was added to 16.46 grams of water in a container with stirring. Glycerin was added to the mixture. In a separate container, acrylic acid, 2,2-dimethoxy-2-phenylacetophenone, and triethyleneglycolbismethacrylate were mixed to dissolution. A solution of 50% by weight water and 50% by weight sodium hydroxide was then added to the acrylic acid solution. The acrylic acid mixture was then mixed with the poly(N-vinylpyrrolidone) mixture and this combined mixture was equilibrated overnight prior to curing. Samples were coated on the aluminum side of an aluminum/polyester laminate, covered with a 1.5 mil polyester film, and cured via ultraviolet light using a series of 15-watt Sylvania 350 nm blacklight bulbs operating at an intensity of 1.2 milliwatts/cm$^2$. The curing conditions were ambient temperature, pressure, and humidity. The curing time was 5 minutes.

Comparison example 12 represents a commercially available electrode and was prepared in the same manner as Examples 5-11 except that no poly(N-vinyl pyrrolidone) was added to the precursor mixture and that water and glycerin from that mixture were added to the acrylic acid mixture before the addition of the sodium hydroxide solution. Coating and curing were the same.

Skin adhesion was measured at initial time ($T_0$) and after four hours ($T_4$) of dwell on human skin according to the Skin Adhesion Test described above.

TABLE 3

| Ingredients (grams) | Ex. 5 | Ex. 6 | Ex. 7 | Ex. 8 | Ex. 9 | Ex. 10 | Ex. 11 | Comparison Example 12 |
|---|---|---|---|---|---|---|---|---|
| Acrylic acid | 17 | 17 | 17 | 17 | 16 | 14 | 15 | 24 |
| 2,2-dimethoxy-2-phenylacetophenone | 0.06 | 0.06 | 0.06 | 0.06 | 0.06 | 0.06 | 0.06 | 0.06 |
| TEGBM | 0.8 | 0.8 | 1.2 | 1.2 | 1.2 | 0.8 | 1.0 | 0.2 |
| Water | 20 | 20 | 20 | 20 | 20 | 20 | 20 | 10.0 |
| NaOH | 3.54 | 3.54 | 3.54 | 3.54 | 3.33 | 2.92 | 3.13 | 5.0 |
| Glycerin | 57.6 | 56.6 | 57.2 | 56.2 | 57.41 | 60.22 | 59.31 | 60.74 |
| Crosslinked PVP | 1 | 2 | 1 | 2 | 2 | 2 | 1.5 | 0 |

TABLE 4

| Property | Ex. 5 | Ex. 6 | Ex. 7 | Ex. 8 | Ex. 9 | Ex. 10 | Ex. 11 | Comparison Example 12 |
|---|---|---|---|---|---|---|---|---|
| Impedance (Ohms/0.0254 mm) | 0.42 | 0.54 | 0.46 | 0.49 | 0.45 | 0.39 | 0.45 | 1.6 |
| Adhesion $T_0$ hours (grams/2.54 cm) | 54.5 | 53.25 | 40.75 | 36.5 | 46.55 | 92.67 | 71.78 | 39.5 |
| Adhesion $T_4$ hours (grams/2.54 cm) | 31 | 36.75 | 26 | 25 | 40.82 | 66.91 | 61.33 | 79.43 |

Mechanical adhesion of Examples 5–11 are superior to adhesion of Comparison Example 12 because adhesion does not build over time. Thus, after an operation or monitoring time lasting about 4 hours, it is easier to remove electrodes having low impedance pressure sensitive adhesive of the present invention than commercially available adhesives. Yet there is sufficient adhesion to retain such electrodes in place on mammalian skin for the duration of the medical procedure. Thus, the addition of crosslinked poly(N-vinyl lactam) to PSA hydrogels according to the present invention provides a superior mechanical property of reduced adhesion over time of use while perspiration and other moisture sorb into such adhesive.

The present invention is not limited to the above embodiments. For an appreciation of the scope of the present invention, the claims follow.

What is claimed is:

1. A low impedance, water-absorbing, ionically-conductive, hydrophilic pressure sensitive adhesive composition, consisting essentially of:
   an ionically-conductive, hydrophilic pressure sensitive adhesive hydrogel comprising a polymer, humectant, and water, and
   radiation crosslinked poly(N-vinyl lactam) homopolymer dispersed as swellable solids in the hydrogel and present in an amount from about 0.5 to about 3.0 weight percent of the composition to retain low electrical impedance and maintain hydrogel adhesion and cohesion during use of the composition in the presence of mammalian body fluids tending to plasticize said hydrogel;
   wherein said hydrogel polymer is selected from the group consisting of
   (a) (1) partially neutralized acrylic acid homopolymers, (2) partially neutralized acrylic acid copolymers, (3) copolymers of N-vinyl lactam and a multi-ethylenically unsaturated compound, (4) copolymers of N-vinyl lactam and a carboxylic acid, and (5) an interpenetrating polymer network of hydrophilic crosslinked polymer from a water soluble monomer and a hydrophilic polymer which is not crosslinked; and
   wherein said radiation crosslinked poly(N-vinyl lactam) homopolymer swellable solids are crosslinked by ionizing radiation prior to dispersion in the hydrogel in a solid state form.

2. The composition according to claim 1, wherein said radiation crosslinked poly(N-vinyl lactam) homopolymer swellable solids are particles of radiation crosslinked poly(N-vinyl-2-pyrrolidone) homopolymer having a Swelling Capacity of at least 15 milliliters of water per gram of radiation crosslinked poly (N-vinyl-2-pyrrolidone) homopolymer.

3. The composition according to claim 2, wherein said radiation crosslinked poly(N-vinyl-2-pyrrolidone) homopolymer swellable solids have a Swelling Capacity of at least 30 milliliters of water per gram of said radiation crosslinked poly(N-vinyl-2-pyrrolidone) homopolymer.

4. The composition according to claim 1, wherein said radiation crosslinked poly(N-vinyl lactam) homopolymer swellable solids are particles of radiation crosslinked poly(N-vinyl-2-pyrrolidone) homopolymer having a Fikentscher K-value of at least K-15.

5. The composition according to claim 1, wherein said radiation crosslinked poly(N-vinyl lactam) homopolymer swellable solids comprise from about 1 to about 2 percent by weight of the composition.

6. The composition according to claim 1, further comprising an iontophoretically active pharmaceutical dispersed in the composition.

* * * * *

UNITED STATES PATENT AND TRADEMARK OFFICE
CERTIFICATE OF CORRECTION

PATENT NO. : 5,362,420
DATED : November 8, 1994
INVENTOR(S) : Itoh et al.

It is certified that error appears in the above-identified patent and that said Letters Patent is hereby corrected as shown below:

Column 4, line 34, "(N-vinyl lactam" should read --N-vinyl lactam--.

Column 4, line 35, "(N-vinyl lactam)" should read -- N-vinyl lactam--.

Signed and Sealed this

Seventh Day of November, 1995

*Attest:*

BRUCE LEHMAN

*Attesting Officer*    *Commissioner of Patents and Trademarks*